(12) United States Patent
Petersen et al.

(10) Patent No.: US 8,372,157 B2
(45) Date of Patent: Feb. 12, 2013

(54) JOINT REVISION IMPLANT

(75) Inventors: Kenneth C. Petersen, Brick, NJ (US);
Thomas Einhorn, Boston, MA (US);
David L. Reed, Syracuse, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 371 days.

(21) Appl. No.: 12/526,871

(22) PCT Filed: Feb. 11, 2008

(86) PCT No.: PCT/US2008/053588
§ 371 (c)(1),
(2), (4) Date: Oct. 14, 2009

(87) PCT Pub. No.: WO2008/100856
PCT Pub. Date: Aug. 21, 2008

(65) Prior Publication Data
US 2010/0049326 A1     Feb. 25, 2010

Related U.S. Application Data

(60) Provisional application No. 60/889,437, filed on Feb. 12, 2007, provisional application No. 60/985,859, filed on Nov. 6, 2007.

(51) Int. Cl.
*A61F 2/28* (2006.01)
(52) U.S. Cl. ............... 623/23.61; 623/23.43; 623/22.21
(58) Field of Classification Search ............... 623/17.18, 623/17.19, 22.11, 22.12, 22.15–22.19, 22.21–22.26, 623/22.35, 23.43, 23.51, 23.61–23.63, 23.72–23.73, 623/18.11, 22.3, 23.46; 606/280, 70, 71, 606/283–285, 298
See application file for complete search history.

(56) References Cited

U.S. PATENT DOCUMENTS

| | | | |
|---|---|---|---|
| 1,025,008 A | | 4/1912 | Miner |
| 1,939,797 A | * | 12/1933 | Swift ..................... 229/400 |
| 2,375,116 A | | 5/1945 | Larkin |
| 2,525,222 A | | 10/1950 | Holt |
| 3,068,916 A | | 12/1962 | Richardson |
| 3,486,505 A | | 12/1969 | Morrison |
| 3,604,298 A | | 9/1971 | Dekiel |
| 3,604,487 A | | 9/1971 | Gilbert |
| 3,707,006 A | | 12/1972 | Bokros et al. |
| 3,848,601 A | | 11/1974 | Ma et al. |
| 4,033,244 A | | 7/1977 | Jacobson |
| 4,059,115 A | | 11/1977 | Jumashev et al. |

(Continued)

FOREIGN PATENT DOCUMENTS

| AU | 744371 | 11/1998 |
|---|---|---|
| DE | 2 253 086 | 10/1972 |

(Continued)

OTHER PUBLICATIONS

Albee, Fred H., "Bone Surgery with Machine Tools," *Scientific American*, Apr. 1936, pp. 178-181.

(Continued)

*Primary Examiner* — David Isabella
*Assistant Examiner* — Suba Ganesan

(57) ABSTRACT

An osteoconductive backing implant for joint revisions is provided that may enhance bone healing and, for cementless implants, bony integration of the implant. The backing implant comprises a generally planar surface that may be formed into a generally hemispherical shape. In one embodiment, the backing implant comprises a disc having an inner hole and an outer edge, at least one slit extending from the inner hole to the outer edge. The disc may be formed from a coherent mass of elongate, mechanically entangled demineralized bone particles.

19 Claims, 7 Drawing Sheets

U.S. PATENT DOCUMENTS

| | | | |
|---|---|---|---|
| 4,185,383 A | 1/1980 | Heimke et al. | |
| 4,273,117 A | 6/1981 | Neuhauser | |
| 4,349,921 A | 9/1982 | Kuntz | |
| 4,394,370 A | 7/1983 | Jefferies | |
| 4,416,278 A | 11/1983 | Miller | |
| 4,440,750 A | 4/1984 | Glowacki et al. | |
| 4,484,570 A | 11/1984 | Sutter et al. | |
| 4,485,097 A | 11/1984 | Bell | |
| 4,516,276 A | 5/1985 | Mittelmeier et al. | |
| 4,553,575 A | 11/1985 | Brown | |
| 4,559,936 A | 12/1985 | Hill | |
| 4,566,466 A | 1/1986 | Ripple et al. | |
| 4,573,448 A | 3/1986 | Kambin | |
| 4,637,931 A | 1/1987 | Schmitz | |
| 4,649,918 A | 3/1987 | Pegg et al. | |
| 4,678,470 A | 7/1987 | Nashef et al. | |
| 4,714,469 A | 12/1987 | Kenna | |
| 4,743,256 A | 5/1988 | Brantigan | |
| 4,743,259 A | 5/1988 | Bolander et al. | |
| 4,753,235 A | 6/1988 | Hasson | |
| 4,772,287 A | 9/1988 | Ray et al. | |
| 4,782,833 A | 11/1988 | Einhorn | |
| 4,798,213 A | 1/1989 | Doppelt | |
| 4,820,305 A | 4/1989 | Harms et al. | |
| 4,834,757 A | 5/1989 | Brantigan | |
| 4,863,477 A | 9/1989 | Monson | |
| 4,877,020 A | 10/1989 | Vich | |
| 4,878,915 A | 11/1989 | Brantigan | |
| 4,904,261 A | 2/1990 | Dove et al. | |
| 4,917,704 A | 4/1990 | Frey et al. | |
| 4,932,973 A | 6/1990 | Gendler | |
| 4,938,768 A | 7/1990 | Wu | |
| 4,950,296 A | 8/1990 | McIntyre | |
| 4,955,885 A | 9/1990 | Meyers | |
| 4,961,740 A | 10/1990 | Ray et al. | |
| 4,963,154 A | 10/1990 | Anapliotis et al. | |
| 4,997,434 A | 3/1991 | Seedhom et al. | |
| 5,015,247 A | 5/1991 | Michelson | |
| 5,015,255 A | 5/1991 | Kuslich | |
| 5,026,373 A | 6/1991 | Ray et al. | |
| 5,047,058 A | 9/1991 | Roberts et al. | |
| 5,049,150 A | 9/1991 | Cozad | |
| 5,053,049 A | 10/1991 | Campbell | |
| 5,055,104 A | 10/1991 | Ray | |
| 5,061,786 A | 10/1991 | Burnier et al. | |
| 5,062,845 A | 11/1991 | Kuslich et al. | |
| 5,098,144 A * | 3/1992 | Marvin | 294/87.2 |
| 5,112,354 A | 5/1992 | Sires | |
| 5,171,278 A | 12/1992 | Pisharodi | |
| 5,192,321 A | 3/1993 | Strokon | |
| 5,192,327 A | 3/1993 | Brantigan | |
| 5,197,967 A | 3/1993 | Wilson | |
| 5,207,710 A | 5/1993 | Chu et al. | |
| 5,236,456 A | 8/1993 | O'Leary et al. | |
| 5,284,655 A | 2/1994 | Bogdansky et al. | |
| 5,298,254 A | 3/1994 | Prewett et al. | |
| 5,306,307 A | 4/1994 | Senter et al. | |
| 5,306,308 A | 4/1994 | Gross et al. | |
| 5,306,309 A | 4/1994 | Wagner et al. | |
| 5,306,310 A | 4/1994 | Siebels | |
| 5,312,408 A | 5/1994 | Brown | |
| 5,314,476 A | 5/1994 | Prewett et al. | |
| 5,314,478 A | 5/1994 | Oka et al. | |
| 5,361,483 A | 11/1994 | Rainville et al. | |
| 5,380,333 A | 1/1995 | Meloul et al. | |
| 5,390,683 A | 2/1995 | Pisharodi | |
| 5,397,364 A | 3/1995 | Kozak et al. | |
| 5,423,817 A | 6/1995 | Lin | |
| 5,423,825 A | 6/1995 | Levine | |
| 5,425,772 A | 6/1995 | Brantigan | |
| 5,425,773 A | 6/1995 | Boyd et al. | |
| 5,439,684 A | 8/1995 | Prewett et al. | |
| 5,443,514 A | 8/1995 | Steffee | |
| 5,445,639 A | 8/1995 | Kuslich et al. | |
| 5,458,638 A | 10/1995 | Kuslich et al. | |
| 5,458,643 A | 10/1995 | Oka et al. | |
| 5,484,437 A | 1/1996 | Michelson | |
| 5,489,307 A | 2/1996 | Kuslich et al. | |
| 5,489,308 A | 2/1996 | Kuslich et al. | |
| 5,490,962 A | 2/1996 | Cima et al. | |
| 5,505,731 A | 4/1996 | Tornier | |
| 5,505,732 A | 4/1996 | Michelson | |
| 5,507,813 A | 4/1996 | Dowd et al. | |
| 5,514,180 A | 5/1996 | Heggeness et al. | |
| 5,518,680 A | 5/1996 | Cima et al. | |
| 5,522,899 A | 6/1996 | Michelson | |
| 5,534,028 A | 7/1996 | Bao et al. | |
| 5,534,030 A | 7/1996 | Navarro et al. | |
| 5,545,222 A | 8/1996 | Bonutti | |
| 5,554,191 A | 9/1996 | Lahille et al. | |
| 5,562,738 A | 10/1996 | Boyd et al. | |
| 5,571,190 A | 11/1996 | Ulrich et al. | |
| 5,571,192 A | 11/1996 | Schonhoffer | |
| 5,591,235 A | 1/1997 | Kuslich | |
| 5,593,409 A | 1/1997 | Michelson | |
| 5,607,269 A | 3/1997 | Dowd et al. | |
| 5,607,424 A | 3/1997 | Tropiano | |
| 5,609,635 A | 3/1997 | Michelson | |
| 5,609,636 A | 3/1997 | Kohrs et al. | |
| 5,632,747 A | 5/1997 | Scarborough et al. | |
| 5,645,596 A | 7/1997 | Kim et al. | |
| 5,645,598 A | 7/1997 | Brosnahan, III | |
| 5,653,761 A | 8/1997 | Pisharodi | |
| 5,653,762 A | 8/1997 | Pisharodi et al. | |
| 5,653,763 A | 8/1997 | Errico et al. | |
| 5,658,336 A | 8/1997 | Pisharodi | |
| 5,658,337 A | 8/1997 | Kohrs et al. | |
| 5,662,710 A | 9/1997 | Bonutti | |
| 5,669,909 A | 9/1997 | Zdeblick et al. | |
| 5,683,394 A | 11/1997 | Rinner | |
| 5,683,463 A | 11/1997 | Godefroy et al. | |
| 5,683,464 A | 11/1997 | Wagner et al. | |
| 5,702,391 A | 12/1997 | Lin | |
| 5,707,371 A | 1/1998 | Metz-Stavenhagen | |
| 5,709,683 A | 1/1998 | Bagby | |
| 5,716,415 A | 2/1998 | Steffee | |
| 5,716,416 A | 2/1998 | Lin | |
| 5,720,751 A | 2/1998 | Jackson | |
| 5,728,159 A | 3/1998 | Stroever et al. | |
| 5,741,253 A | 4/1998 | Michelson | |
| 5,749,916 A | 5/1998 | Richelsoph | |
| 5,766,251 A | 6/1998 | Koshino | |
| 5,766,252 A | 6/1998 | Henry et al. | |
| 5,769,897 A | 6/1998 | Harle | |
| 5,776,199 A | 7/1998 | Michelson | |
| 5,782,830 A | 7/1998 | Farris | |
| 5,782,919 A | 7/1998 | Zdeblick et al. | |
| 5,785,710 A | 7/1998 | Michelson | |
| 5,800,547 A | 9/1998 | Schafer et al. | |
| 5,807,437 A | 9/1998 | Sachs et al. | |
| 5,814,084 A | 9/1998 | Grivas et al. | |
| 5,824,078 A | 10/1998 | Nelson et al. | |
| 5,824,094 A | 10/1998 | Serhan et al. | |
| 5,846,484 A | 12/1998 | Scarborough et al. | |
| 5,860,973 A | 1/1999 | Michelson | |
| 5,865,845 A | 2/1999 | Thalgott | |
| 5,868,749 A | 2/1999 | Reed | |
| 5,885,299 A | 3/1999 | Winslow et al. | |
| 5,885,300 A | 3/1999 | Tokuhashi et al. | |
| 5,888,219 A | 3/1999 | Bonutti | |
| 5,888,222 A | 3/1999 | Coates | |
| 5,888,227 A | 3/1999 | Cottle | |
| 5,895,426 A | 4/1999 | Scarborough et al. | |
| 5,895,428 A | 4/1999 | Berry | |
| 5,899,939 A | 5/1999 | Boyce et al. | |
| 5,904,683 A | 5/1999 | Pohndorf et al. | |
| 5,904,719 A | 5/1999 | Errico et al. | |
| 5,928,238 A | 7/1999 | Scarborough et al. | |
| 5,941,882 A | 8/1999 | Jammet et al. | |
| 5,968,047 A | 10/1999 | Reed | |
| 5,972,368 A | 10/1999 | McKay | |
| 5,980,522 A | 11/1999 | Koros et al. | |
| 5,984,967 A | 11/1999 | Zdeblick et al. | |
| 5,989,289 A | 11/1999 | Coates et al. | |
| 6,004,353 A * | 12/1999 | Masini | 623/22.21 |
| 6,025,538 A | 2/2000 | Yaccarino, III | |
| 6,030,635 A | 2/2000 | Gertzman et al. | |

| | | | | | | |
|---|---|---|---|---|---|---|
| 6,045,554 | A | 4/2000 | Grooms et al. | 2005/0283255 A1 | 12/2005 | Geremakis et al. |
| 6,045,579 | A | 4/2000 | Hochshuler et al. | 2006/0149376 A1 | 7/2006 | Shimp et al. |
| 6,045,580 | A | 4/2000 | Scarborough et al. | 2007/0178158 A1 | 8/2007 | Knaack et al. |
| 6,066,174 | A | 5/2000 | Farris | | | |
| 6,077,267 | A | 6/2000 | Huene | FOREIGN PATENT DOCUMENTS | | |
| 6,083,225 | A | 7/2000 | Winslow et al. | DE | 40 12 622 C | 7/1991 |
| 6,090,143 | A | 7/2000 | Meriwether et al. | DE | 43 02 397 | 7/1993 |
| 6,096,081 | A | 8/2000 | Grivas et al. | DE | 198 15 407 | 10/1999 |
| 6,102,950 | A | 8/2000 | Vaccaro | DE | 298 14 174 U | 12/1999 |
| 6,111,164 | A | 8/2000 | Rainey et al. | EP | 0 302 719 | 2/1989 |
| 6,113,637 | A | 9/2000 | Gill et al. | EP | 0 307 241 | 3/1989 |
| 6,113,638 | A | 9/2000 | Williams et al. | EP | 0 325 566 | 7/1989 |
| 6,123,705 | A | 9/2000 | Michelson | EP | 0 332 826 | 9/1989 |
| 6,123,731 | A | 9/2000 | Boyce et al. | EP | 0 493 698 | 7/1992 |
| 6,132,470 | A * | 10/2000 | Berman .................... 623/23.15 | EP | 0 732 093 | 2/1996 |
| 6,132,472 | A | 10/2000 | Bonutti | EP | 0 734 703 | 10/1996 |
| 6,136,002 | A | 10/2000 | Shih et al. | EP | 1 064 890 | 1/2001 |
| 6,139,211 | A | 10/2000 | Schroeder et al. | FR | 2636227 | 3/1990 |
| 6,143,033 | A | 11/2000 | Paul et al. | FR | 2703580 | 10/1994 |
| 6,156,037 | A | 12/2000 | LeHuec et al. | FR | 2742652 | 6/1997 |
| 6,159,215 | A | 12/2000 | Urbahns et al. | FR | 2769827 | 4/1999 |
| 6,174,311 | B1 | 1/2001 | Branch et al. | JP | 01/179689 | 7/1989 |
| 6,200,347 | B1 | 3/2001 | Anderson et al. | SU | 1107854 | 8/1984 |
| 6,206,923 | B1 | 3/2001 | Boyd et al. | SU | 590872 A | 11/1985 |
| 6,210,442 | B1 | 4/2001 | Wing et al. | WO | WO 89/09035 | 10/1989 |
| 6,235,059 | B1 | 5/2001 | Benezech et al. | WO | WO 93/01771 | 2/1993 |
| 6,258,125 | B1 | 7/2001 | Paul et al. | WO | WO 94/21298 | 9/1994 |
| 6,270,528 | B1 | 8/2001 | McKay | WO | WO 97/15246 | 5/1997 |
| 6,277,149 | B1 | 8/2001 | Boyle et al. | WO | WO 97/47258 | 12/1997 |
| 6,294,041 | B1 | 9/2001 | Boyce et al. | WO | WO 98/02117 | 1/1998 |
| 6,294,187 | B1 | 9/2001 | Boyce et al. | WO | WO 98/17209 | 4/1998 |
| 6,315,795 | B1 | 11/2001 | Scarborough et al. | WO | WO 98/48738 | 11/1998 |
| 6,326,018 | B1 | 12/2001 | Gertzman et al. | WO | WO 99/07312 | 2/1999 |
| 6,350,283 | B1 | 2/2002 | Michelson | WO | WO 99/09914 | 3/1999 |
| 6,379,385 | B1 | 4/2002 | Kalas et al. | WO | WO 99/21515 | 5/1999 |
| 6,383,221 | B1 | 5/2002 | Scarborough et al. | WO | WO 99/38461 | 8/1999 |
| 6,425,920 | B1 | 7/2002 | Hamada | WO | WO 00/07527 | 2/2000 |
| 6,432,107 | B1 | 8/2002 | Ferree | WO | WO 00/24327 | 5/2000 |
| 6,454,806 | B1 | 9/2002 | Cohen et al. | WO | WO 00/40177 | 7/2000 |
| 6,468,543 | B1 | 10/2002 | Gilbertson et al. | WO | WO 00/40179 | 7/2000 |
| 6,527,773 | B1 | 3/2003 | Lin et al. | WO | WO 01/00792 | 1/2001 |
| 6,530,955 | B2 | 3/2003 | Boyle et al. | WO | WO 01/49220 | 7/2001 |
| 6,547,823 | B2 | 4/2003 | Scarborough et al. | WO | WO 01/66048 | 9/2001 |
| 6,569,168 | B2 | 5/2003 | Lin | WO | WO 01/70136 | 9/2001 |
| 6,579,321 | B1 | 6/2003 | Gordon et al. | WO | WO 01/70137 | 9/2001 |
| 6,638,310 | B2 | 10/2003 | Lin et al. | WO | WO 01/70139 | 9/2001 |
| 6,696,073 | B2 | 2/2004 | Boyce et al. | WO | WO 01/78798 | 10/2001 |
| 6,733,504 | B2 | 5/2004 | Lin et al. | WO | WO 03/030956 A2 | 4/2003 |
| 6,855,167 | B2 | 2/2005 | Shimp et al. | WO | WO 2005/072656 | 8/2005 |
| 6,863,694 | B1 * | 3/2005 | Boyce et al. ............... 623/23.63 | | | |
| 6,911,045 | B2 | 6/2005 | Shimp | OTHER PUBLICATIONS | | |
| 2001/0020186 | A1 | 9/2001 | Boyce et al. | | | |
| 2001/0043258 | A1 | 11/2001 | Ohki | | | |
| 2002/0029084 | A1 | 3/2002 | Paul et al. | | | |
| 2002/0045897 | A1 | 4/2002 | Dixon et al. | | | |
| 2002/0058950 | A1 | 5/2002 | Winterbottom et al. | | | |
| 2002/0128717 | A1 | 9/2002 | Alfaro et al. | | | |
| 2002/0161445 | A1 | 10/2002 | Crozel | | | |
| 2002/0188295 | A1 | 12/2002 | Martz et al. | | | |
| 2003/0039676 | A1 | 2/2003 | Boyce et al. | | | |
| 2003/0049326 | A1 | 3/2003 | Nimni | | | |
| 2003/0060825 | A1 | 3/2003 | Alfaro et al. | | | |
| 2003/0130667 | A1 | 7/2003 | Lin | | | |
| 2003/0135214 | A1 | 7/2003 | Fetto et al. | | | |
| 2003/0147860 | A1 | 8/2003 | Marchosky | | | |
| 2004/0024457 | A1 | 2/2004 | Boyce et al. | | | |
| 2004/0044409 | A1 | 3/2004 | Alfaro et al. | | | |
| 2004/0098129 | A1 | 5/2004 | Lin | | | |
| 2004/0146543 | A1 | 7/2004 | Shimp et al. | | | |
| 2004/0243242 | A1 | 12/2004 | Sybert et al. | | | |
| 2004/0249377 | A1 | 12/2004 | Kaes et al. | | | |
| 2005/0008620 | A1 | 1/2005 | Shimp et al. | | | |
| 2005/0008672 | A1 | 1/2005 | Winterbottom et al. | | | |
| 2005/0027033 | A1 | 2/2005 | Knaack et al. | | | |
| 2005/0038511 | A1 | 2/2005 | Martz et al. | | | |
| 2005/0107880 | A1 | 5/2005 | Shimp et al. | | | |
| 2005/0143740 | A1 | 6/2005 | Morris et al. | | | |

OTHER PUBLICATIONS

*Allograft Freeze-Dried Release Specifications,* Osteotech, Inc., Sep. 30, 1992, 3 pages.

Brantigan, J.W., DePuy AcroMed, Lumbar I/F Cage With VSP Spinal System (Surgical Technique) (1999).

Crowe et al., "Inhibition of Enzymatic Digestion of Amylose by Free Fatty Acids in Vitro Contributes to Resistant Starch Formation", J. Nutr. 130(8): 2006-2008, 2000.

DePuy AcroMed, Lumbar I/F Cage Implants & Instruments (Product Catalog) (1999).

Driessens et al., "Calcium phosphate bone cements," *Universitat Politecnica de Catalunya,* Barcelona, Spain, 31: 855-77.

Edwards et al., "Osteoinduction of Human Demineralized Bone: Characterization in Rat Model", Clinical Orthopaedics and Related Research, No. 357, pp. 219-228 (1998).

Frymoyer et al., Eds., "The Adult Spine Principles and Practice," *Poster Lumbar Interbody Fusion,* James W. Simmons, vol. 2, pp. 1961-1987 (1991).

Gerhart et al. "Biomechanical optimization of a model particulate composite for orthopaedic applications," *J. Orthop. Res* (1986); 4(1): 86-85 [abstract only].

Glowacki et al., "Fate of Mineralized and Demineralized Osseous Implants in Cranial Defects", Calcified Tissue Int. 33: 71-76, 1981.

Glowacki et al., "Demineralized Bone Implants", Symposium on Horizons in Plastic Surgery, vol. 12, No. 2, pp. 233-241 (1985).

Han et al. "Quantitative and sensitive in vitro assay for osteoinductive activity of demineralized bone matrix," J. Orthop. Res., 21(4): 648-54, 2003.

Jain et al., "Anchoring of phospholipase A2: the effect of anions and deuterated water, and the role of N-terminus region," *Biochem. et Biophys. Acta*, 860:448-61, 1986.

Katz, "The biology of heavy water," *Scientific American*, 106-116, 1960.

Lewandrowski et al., "Improved Osteoinduction of Cortical Bone Allografts: A Study of the Effects of Laser Perforation and Partial Demineralization," *J. Ortho Res.* 15:748-756 (1997).

Ma, G.W.C., Posterior Lumbar Interbody Fusion with Specialized Instruments, *Clinical Ortho and Rel. Res.*, 193 (March) pp. 57-63 (1985).

McCord et al., "Anterior endoscopic thoracolumbar instrumentation and implants," *Curr. Ortho 12*, pp. 96-103 (1998).

MTF Bone Catalog, Fibular Wedges, Femoral Struts, Tibial Struts, published prior to 2000, 1 page.

Neigal et al., "Use of Demineralized Bone Implants in Orbital and Craniofacial", Opthal. Plast. Reconstrs. Surg., 12: 108-120, 1996.

Ray et al., "Preliminary Report of an Experimental Study", J. Bone Joint Surgery, 39 A: 1119-1128, 1957.

Russell et al., "Clinical Utility of Demineralized Bone Matrix for Osseous Defects, Arthrodesis and Reconstruction: Impact of Processing Techniques and Study Methodology", Orthpaedics, 22(5): 524-531, 1999.

Smith, MD et al. "Load-bearing capacity of corticocancellous bone grafts in the spine" (truncated abstract), Aug. 1993, *Journal of Bone & Joint Surgery*, 75(8): 1206-13.

Sofamar Danek, "Surgical Technique Using Bone Dowel Instrumentation for Anterior Approach" [Publication Date Unknown].

Stevenson, S., "Enhancement of Fracture Healing with Autogenous and Allogeneic Bone Grafts," *Clin. Ortho, Rel. Res.* 355S, pp. S239-S246 (1998).

Tan et al., A modified technique of anterior Lumbar fusion with femoral cortical allograft; *J. Orthop. Surg. Tech;* vol. 5, No. 3 91990), pp. 83-93.

Ueland et al., "Increased Cortical Bone Content of Insulin-Like Growth Factors in Acromegalic Patients", J. Clin. Endocrinol. Metab., 84(1): 123-127, 1999.

University of Florida Tissue Bank, Inc., Allograft Catalog [Publication Date Unknown].

University of Florida Tissue Transplant Patient Education Series [Publication Data Unknown].

Urist et al., "Observations implicating an extracellular enzymic mechanism of control of bone morphogenesis," *J. Histochem & Cytochem*, 22(2): 88-103, 1974.

Urist et al., "Preservation and biodegradation of the morphogenetic property of bone matrix," *J. Theor. Biol.* 38: 155-67, 1973.

Urist, "Bone: Formation by Autoinduction", Science, 150: 893-899, 1965.

VG2 Interbody Bone Grafts, DuPuy AcroMed, 2000, 6 pages.

Vich, Jose M. Otero, "Anterior cervical interbody fusion with threaded cylindrical bone," *J. Neurosurg.* 63:750-753, 1985.

Whiteman et al., "Demineralized Bone Powder—Clinical Applications for Bone Defects of the Hand", J. Hand. Surg., 18B: 487-490, 1993.

Whittaker et al., "Matrix Metalloproteinases and Their Inhibitors—Current Status and Future Challenges", Celltransmissions, 17(1): 3-14.

Xiabo et al., "Experimental and Clinical Investigations of Human Insoluble Bone Matrix Gelatin", Clin. Orthrop. 293: 360-365, 1993.

Zhang, et al., "A Quantative Assessment of Osteoinductivity of Human Demineralized Bone Matrix", J. Periodontol. 68(11): 1076-1084, 1997.

\* cited by examiner

JOINT REVISION IMPLANT

This application is a National Stage under 35 U.S.C. 371 of PCT Application No. PCT/US2008/053588, filed on Feb. 11, 2008, which claims priority to U.S. Application No. 60/889,437, filed Feb. 12, 2007, and to U.S. Application No. 60/985,859, filed Nov. 6, 2007, all of which are incorporated herein by reference.

FIELD

A backing implant for joint revisions is provided. More specifically, an osteoconductive backing implant for joint revisions is provided.

BACKGROUND

Overview of Bone Grafts

The rapid and effective repair of bone defects caused by injury, disease, wounds, or surgery has long been a goal of orthopaedic surgery. Toward this end, a number of compositions and materials have been used or proposed for use in the repair of bone defects. The biological, physical, and mechanical properties of the compositions and materials are among the major factors influencing their suitability and performance in various orthopaedic applications.

Much effort has been invested in the identification and development of alternative bone graft materials. Urist has published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material, in that it induces bone growth when implanted in an ectopic site of a rodent, owing to the osteoinductive factors contained within the DBM. Honsawek et al. (2000).

DBM implants have been reported to be particularly useful (see, for example, U.S. Pat. Nos. 4,394,370, 4,440,750, 4,485,097, 4,678,470, and 4,743,259; Mulliken et al., *Calcif Tissue Int.* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993, each of which is incorporated herein by reference). DBM typically is derived from cadavers. The bone is removed aseptically and treated to kill any infectious agents. The bone is particulated by milling or grinding, and then the mineral component is extracted by various methods, such as by soaking the bone in an acidic solution. The remaining matrix is malleable and can be further processed and/or formed and shaped for implantation into a particular site in the recipient. Demineralized bone prepared in this manner contains a variety of components including proteins, glycoproteins, growth factors, and proteoglycans. Following implantation, the presence of DBM induces cellular recruitment to the site of injury. The recruited cells may eventually differentiate into bone forming cells. Such recruitment of cells leads to an increase in the rate of wound healing and, therefore, to faster recovery for the patient.

Overview of Total Hip Joint Replacement Arthroplasty

Total hip joint replacement arthroplasty can provide a patient with dramatically improved quality of life by relieving pain and offering increased mobility. Total hip joint replacement arthroplasty is a surgical procedure wherein diseased portions of the hip joint are removed and replaced with artificial prostheses, such as a femoral component and an acetabular cup. The acetabular cup is fitted in or against the acetabulum. It is noted that the acetabulum comprises the ilium, the ischium, and the pubis. These bones are fused at the acetabulum. For ease of reference, the acetabulum will be discussed as a single structure. Successful replacement of deteriorated, arthritic, or severely injured hips has contributed to enhanced mobility and comfortable, independent living for many people who would otherwise be substantially disabled.

There generally are two broad classes of joint arthroplasty procedures: primary joint replacement arthroplasty and revision arthroplasty. Primary joint replacement is when the original, biological joint is removed and replaced with an implant. Revision arthroplasty is when the primary joint replacement fails and must be replaced.

A failed prosthesis and/or dislocation of a total hip replacement generally causes pain, reduces the ability to work, and necessitates a revision operation. Prosthesis failure and/or dislocations can result from a variety of causes, such as soft tissue laxity, loosening of the implant, and impingement of the femoral neck with either the rim of an acetabular cup implant or the soft tissue or bone surrounding the implant. Loosening of the implant is often due to bone loss around the implant, caused by adverse tissue reactions to wear particles.

Revision arthroplasty involves additional challenges over primary joint replacement because, in addition to placement of the revision implant, the primary implant must be removed. A common problem with revision arthroplasty is a loss of bone stock associated with the removal of bone cement, or osteolysis due to wear debris and the body's reaction to it, or from stress shielding, or a combination of these. Further, in some instances, upon insertion into the acetabulum of an implant, voids may remain between the back surface of the implant and the pelvic bone remaining in the acetabulum. In cases where there is a defect in the area of the acetabulum, or behind the acetabulum, the surgeon will often wish to fill the defect in some way. Bone graft material is sometimes applied to the acetabulum to encourage bone growth between the acetabulum and the acetabular cup. Frequently, the bone graft material falls through voids in the acetabulum.

Commonly, the acetabular cup prosthesis is manufactured of a polymeric material, such as polyethylene. A backing is commonly placed between the acetabular cup prosthesis and the acetabulum. In the past, metal backings have been widely used, at least in part because a stiff backing was believed to be mechanically favorable. It has more recently been determined that a stiff backing causes two problems: It generates higher stress peaks around the acetabular rim than those caused by full polyethylene cups, and it reduces the stresses transferred to the dome of the acetabulum, causing stress shielding.

It would be useful to provide a backing for an acetabular cup prosthesis using bone graft materials such that the prosthesis aids in holding graft material in place, encourages bone apposition up to the implant or, in the case of an implant with a porous metallic coating, encourages ingrowth and biological attachment to the implant.

BRIEF SUMMARY

An osteoconductive backing implant for joint revisions is provided that may enhance bone healing and, for cementless implants, bony integration of the implant.

In one embodiment, the backing implant comprises a disc having an inner hole and an outer edge, at least one slit extending from the inner hole to the outer edge. The disc may be formed from a coherent mass of elongate, mechanically entangled demineralized bone particles.

In another embodiment, the backing implant comprises a disc that has at least one slit extending from an interior of the disk to the outer edge. The disc further includes at least one perforation by which the size or shape of the disc may be manipulated. The disc may be shaped into a cone.

In a further embodiment, the backing implant comprises a sheet of material having a center and a plurality of petals. The sheet of material may be partially folded in on itself by manipulating the petals toward one another.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION

DEFINITIONS

Figure 1:
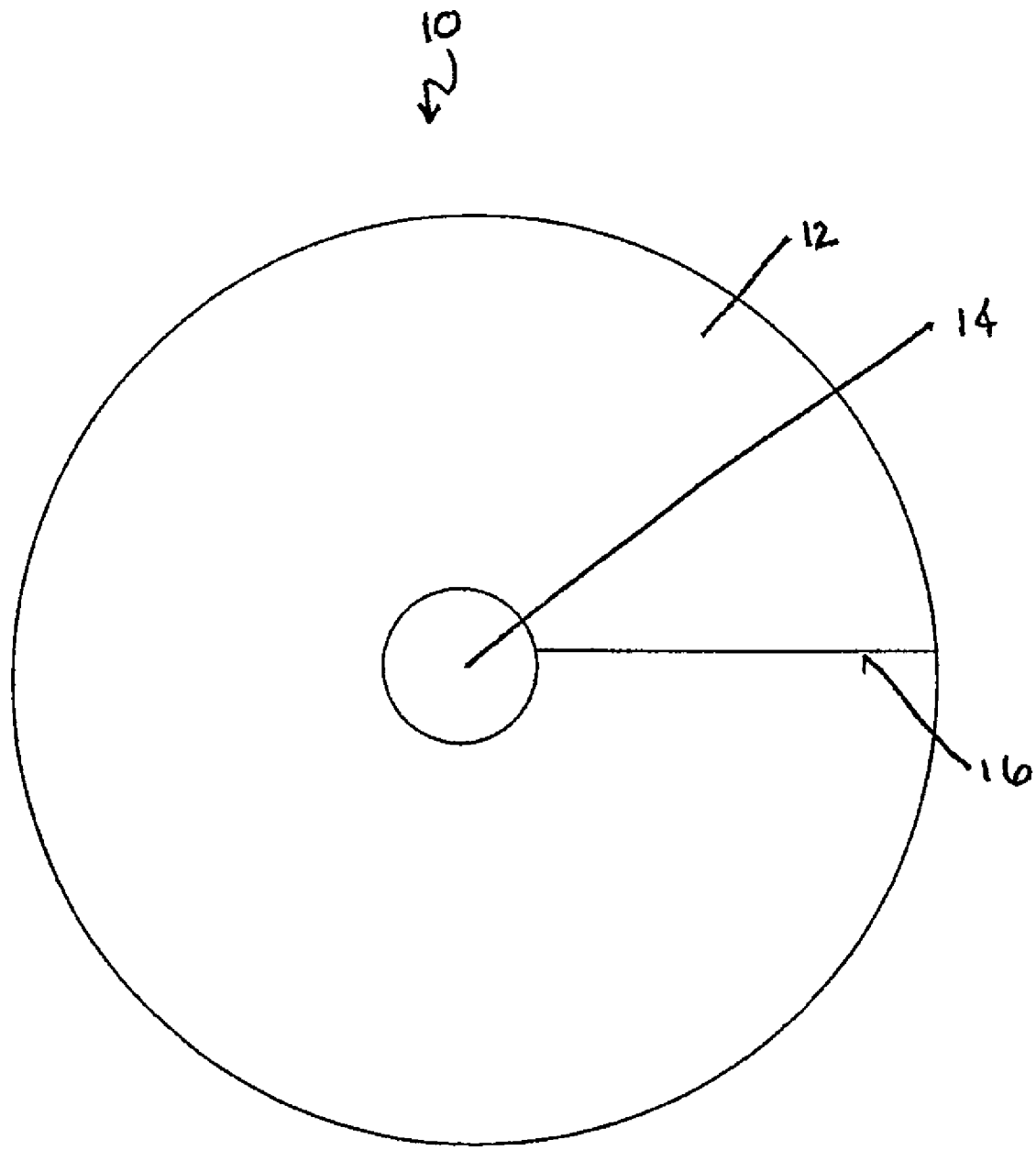
FIG. 1 illustrates a backing implant comprising a disc having a center hole and an outer edge, and a slit extending from the center hole to the outer edge, in accordance with one embodiment.

Biocompatible, as used herein, is intended to describe materials that, upon administration in vivo, do not induce undesirable long-term effects.

Bone as used herein refers to bone that is cortical, cancellous or cortico-cancellous, of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," "fully demineralized," "surface demineralized," etc.

Demineralized bone matrix, as used herein, refers to any material generated by removing mineral material from bone tissue. In some embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Osteoconductive is used herein to refer to the ability of a non-osteoinductive substance to serve as a suitable template or substance along which bone may grow.

Osteogenic is used herein to refer to the ability of an agent, material, or implant to enhance or accelerate the growth of new bone tissue by one or more mechanisms such as osteogenesis, osteoconduction, and/or osteoinduction.

Osteoimplant as used herein refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.,* 357:219-228, December 1998, incorporated herein by reference. In other instances, osteoinduction is considered to occur through cellular recruitment and induction of the recruited cells to an osteogenic phenotype.

Superficially demineralized as used herein refers to bone-derived elements possessing at least about 90 weight percent of their original inorganic mineral content. The expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

I. Introduction

A backing implant for joint revisions is provided that may enhance bone healing. The backing implant may generally be used in reconstruction of a joint, including concave or convex joint surfaces. For the purposes of description, reference is made herein to replacement of the acetabulum. It is to be appreciated, however, that the backing implant described herein may be used in other joint replacements such as replacement of a speroidal joint (also referred to as a "ball and socket joint"), an ellipsoid joint, a sellar joint (also referred to as a "saddle joint"), a bicondular joints, or any joint having a concavity with a defect and a mating convex surface. The present invention may be beneficially used in a variety of joint configurations; see Williams, P. L. and Warwick, R., Gray's Anatomy. 36th ed., Livingstone, Edinburgh (1980), which is hereby incorporated by reference. In some embodiments, the backing implant may be placed in the concavity of the joint.

For cementless implants, such as cementless acetabular cups, the backing implant may enhance bony integration of the implant. When used in a concavity, such as in an acetabular cup, the backing implant accentuates the concavity and offers a possibility of adhesion around the outer perimeter of the concavity. Generally, the backing implant may be fit to the joint surface such that it fills voids or defects in the joint surface. The backing implant may be used with bone, such as autograft bone or allograft bone. More specifically, bone may placed between the backing implant and the implant, such as the acetabular cup, the backing implant substantially preventing bone graft from falling through voids or defects in the joint surface. After implantation, the backing implant may be remodeled and wholly or partially replaced by bone. Thus, in various embodiments, the backing implant fulfills mechanical and bone forming functions. As noted, the backing implant may be used in revision of any suitable joint articulations, such as the shoulder joint, for example being fitted in the glenoid cavity of the scapula. Thus, while this description refers specifically ball-and-socket joints, and more specifically to acetabular cups, one skilled in the art will be able to modify the backing implant to fit other joints.

In accordance with some embodiments, the backing implant comprises a sheet of material that may be shaped to generally form to the joint surface prior to implantation. The sheet may be flexible and/or conformable such that it may conform to irregularities in the bone, for example in the bone of the acetabulum. Such flexibility or conformability permits achieving an increased degree of contact. In some embodiments, the backing implant may comprise a material that is osteoconductive and, possibly, osteoinductive, several examples of which are described below.

Generally, during the healing phase of total joint replacement arthroplasty, the backing implant may not act as the sole weight bearing component. Accordingly, the backing implant may be used with another implant. For example, in a total hip replacement arthroplasty, the backing implant may be used with an acetabular cup, the acetabular cup contacting sufficient host bone to provide support.

The backing implant may be press-fit into the joint, such as in the concavity of a joint, or may be fit around an implant, such as an acetabular cup, prior to its implantation. When press-fit into the joint, it may be desirable to effect pressing using a trial implant or using an implant that will be implanted. In some embodiments, the backing implant may be treated to impart additional stickiness to a portion of the backing implant coming into contact with the joint. The backing implant may be formed of a flexible material, may be formed of a rigid material, a semi-rigid or semi-flexible material, or a material that is rigid but can be made flexible. If the backing implant is formed of a material that is rigid but can be made flexible, the backing implant may be fit in the joint in the flexible state and allowed to become rigid before implanting the implant. Alternatively, the backing implant may remain flexible when the implant is implanted.

As previously noted, bone graft may be used with the backing implant. For example, the bone may comprise morselized allograft, autograft, or other suitable bone material. In use, the backing implant may be placed in the joint, such as in the acetabulum, for example via press fitting with an upper surface of the backing implant being thus provided for receiving an implant. Bone graft, for example morselized allograft, may be provided on the upper surface of the backing implant, before or after placement of the backing implant in the joint. The backing implant substantially prevents the morselized allograft from penetrating into joint, for example from penetrating the joint, for example, in hip arthroplasty, from penetrating the acetabulum and the pelvis. More specifically, the backing implant acts as a barrier to morselized allograft from falling into or through voids or defects in the joint surface. The backing implant works in conjunction with the morselized allograft through osteoinductive and/or osteoconductive properties to form new bone. In an alternative embodiment, autograft bone may be provided on the upper surface of the backing implant before or after placement of the backing implant in the joint. In alternative embodiments, other materials may be provided on the upper surface of the backing implant to aid in bone forming function.

Acetabular cups used in total hip joint replacement arthroplasty may be press-fit or may be cemented in place, for example using methacrylate bone cement. Often, press-fit cups are preferred because of possible bone-to-implant bonding. Using the backing implant provided herein, bone-to-implant bonding is enhanced; the backing implant closely molding to both the acetabulum and the acetabular cup and being osteoconductive, and possibly osteoinductive. Thus, the backing implant enables bone to be induced or conducted from the acetabulum to the acetabular cup.

II. Implant Shapes

Figure 2:
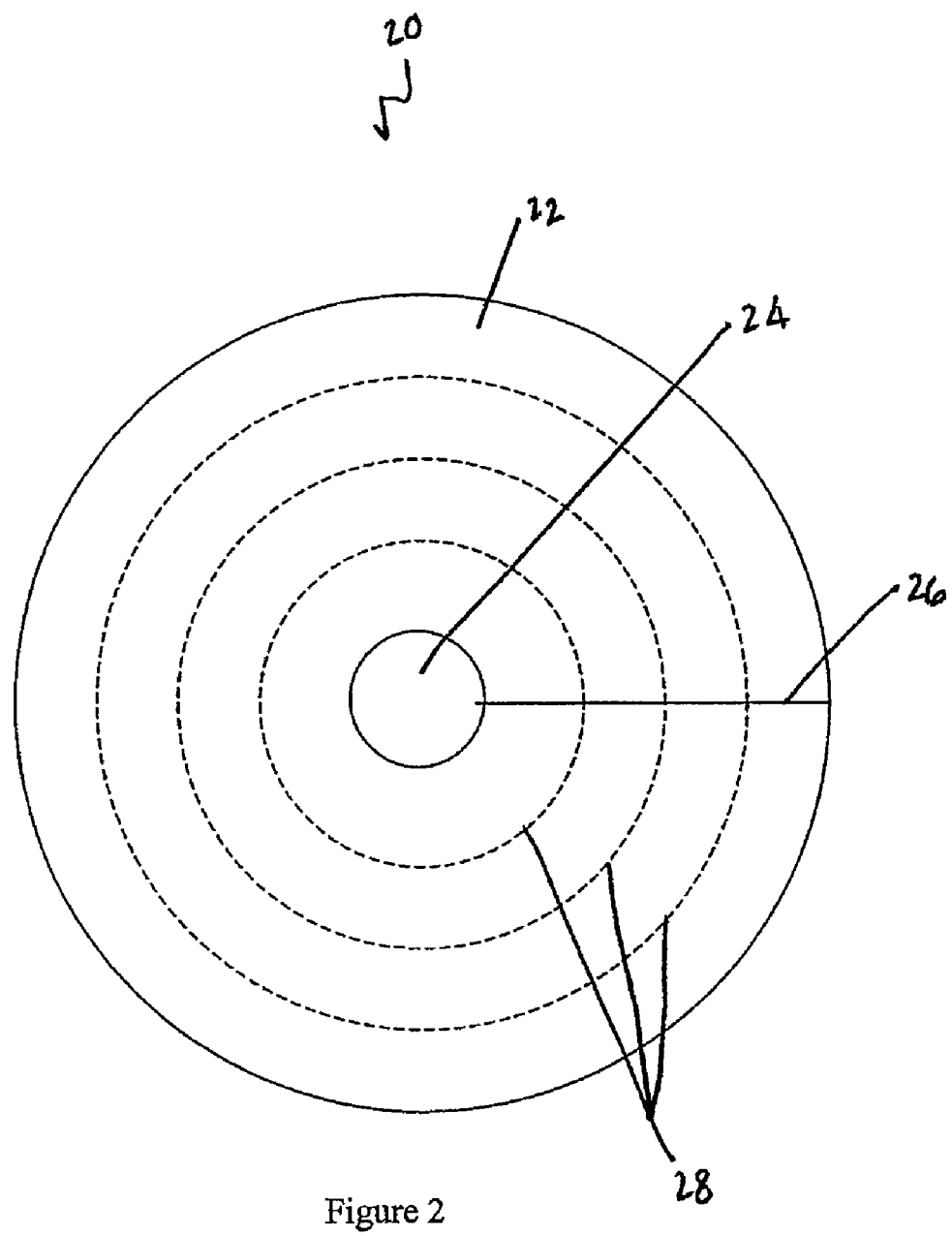
FIG. 2 illustrates a backing implant comprising a disc having a center hole and an outer edge, a slit extending from the center hole to the outer edge, and further comprising a series of generally concentric perforations, in accordance with one embodiment.
Figure 3:
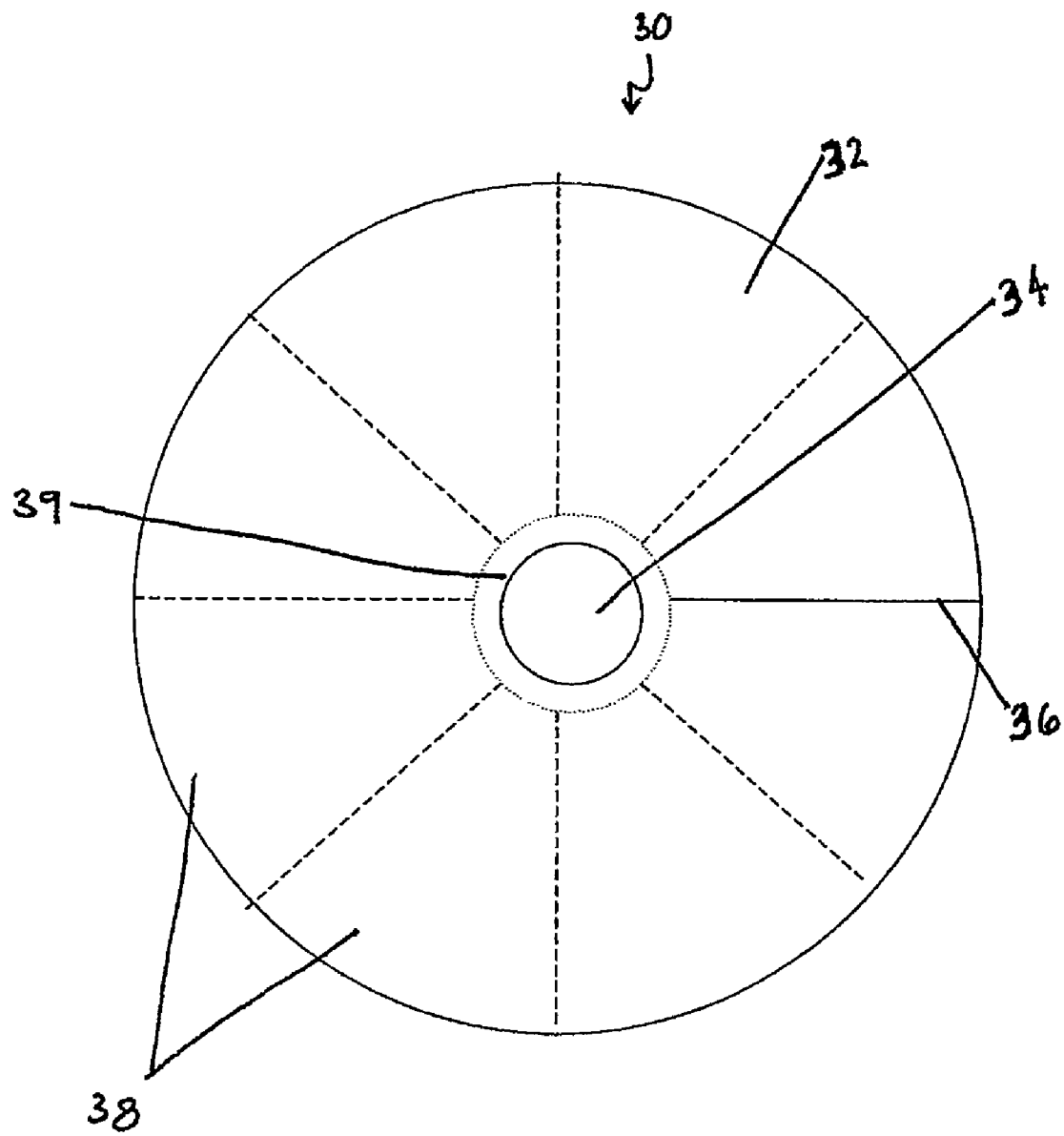
FIG. 3 illustrates a backing implant comprising a disc having a center hole and an outer edge, a slit extending from the center hole to the outer edge, and further comprising a series of wedges, in accordance with one embodiment.

The backing implant may be initially formed as a flat sheet of material The flat sheet of material may, in some embodiments, be formed of one or more layers. The backing implant may be preshaped, may be partially preshaped (described below), or may be shaped by a surgeon for implantation. Generally, the backing implant may be shaped such that, when formed, it is generally complementary to the portion of the joint against which it will be placed. In the embodiments of FIGS. 1-3, the backing implant is described as having a generally conical shape. Thus, in the embodiments shown, the backing implant includes surfaces extending from a base towards an apex. As shown, the backing implant may not extend fully to the apex and thus may comprise a frustum or truncated cone. Further, while the backing implant is shown as a truncated right circular cone, the backing implant may have other conical shapes, such as an elliptical cone, an oblique cone, or other, or non-conical shapes, as appropriate for a given application.

In a first embodiment, shown in FIG. 1, the backing implant 10 comprises a generally circular sheet 12 having a hole 14. The size, shape, and placement of the hole may be varied. For example, the hole may be centered or may be eccentric, may be circular or may be ovoid, etc. The size, shape, and placement of the hole may be determined based on, for example, concavity of the joint surface. In some embodiments, the hole facilitates folding or shaping the backing implant into a cone, described below. In these embodiments, the hole is sized for such use, generally reducing material that may need to be trimmed at the point of the cone and reducing the likelihood of the backing implant wrinkling during folding. In the figures, the generally circular sheet 12 and the center hole 14 are depicted as being round. It is to be understood, however, that, for the embodiment of FIG. 1 as well as all other embodiments described herein, any suitable geometry may be used for the sheet 12, the hole 14, or both, including oval, etc., and, furthermore, that the hole 14 may be placed in any desired location, and need not be at, or over, the center of the generally circular sheet 12. The shape of the implant thus may broadly be referred to as a disc. The sheet 12 and hole 14 may be of any suitable or desired dimensions. In one embodiment, the sheet 12 has an outer diameter of approximately 70 mm and the hole 14 has an inner diameter of approximately 5 mm. Other sizes, for example outer diameters of 30 mm, 45 mm, or 60 mm, may alternatively be provided. In addition, the height or thickness of the implant, i.e., the distance between the upper surface and the lower surface, may be any desired dimension. A slit 16 extends from the hole to the outer edge. The slit 16 may be a straight, clean line and may be perforated or may be cut through. The slit 16 also may be curved, zig-zag, wavy, v-shaped, or any other desired configuration. Using the embodiment of FIG. 1, the surgeon may fold the sheet 12 into a cone shape, thereby correlating the sheet 12 with the interior surface of the acetabular cup. The cut ends of the backing implant, corresponding with the slit 16, may be folded over one another, thus permitting a wide variety of diameters of the cone shape. Further, the overlapping edges may be cut and removed.

In a second embodiment, shown in FIG. 2, the backing implant 20 comprises a generally circular sheet 22 having a hole 24 and a slit 26 extending from the hole to the outer edge, as in the embodiment of FIG. 1. The slit 26 may be perforated or may be cut through. The backing implant 20 of FIG. 2 further includes a series of generally concentric perforations 28. The surgeon may select one of the generally concentric perforations 28 corresponding to a desired outer diameter of the generally circular sheet 22. The surgeon then may tear or cut along the generally concentric perforation 28, removing material between the generally concentric perforation 28 and the outer edge, thereby forming an implant of desired size. As with the embodiment of FIG. 1, the surgeon may then fold the sheet 22 into a cone shape. Further, the overlapping edges may be cut and removed. While the generally concentric perforations 28 are depicted as being round, it is to be understood that any desired geometry may be used. In one embodiment, the perforations may be elliptical. Furthermore, the primary axes of the elliptical perforations may intersect, so that the perforations of the ellipses themselves intersect, thus allowing greater flexibility in the removal of shapes to be generated by the removal of pre-perforated sections. In a variation of the embodiment of FIG. 2, the generally circular sheet 22 may be provided without a hole 24, in which case the slit 26 extends into the interior of the generally circular sheet 22.

FIG. 3 illustrates a further embodiment of a backing implant 30. In the embodiment of FIG. 3, the backing implant 30 comprises a generally circular sheet 32 having a hole 34. A series of wedges 38 are formed between the center hole and the outer edge of the sheet. The wedges 38 may be perforated or may be cut through. In one embodiment, a relatively thin, breakable segment 39 is provided around the center hole 34 connecting the wedges 38. In a variation of the embodiment of FIG. 3, the generally circular sheet 32 is provided without a hole 34. The surgeon may remove one or more wedges 38 to modify the sizing of the backing implant 30 as formed into a cone shape. One or more wedges 38 may be removed when a smaller cone shape is desired, thus less overlapping of the sheet 32 may be required. The wedges 38 may be provided in any desired shape or number. In further embodiments, the backing implant 30 may have both concentric perforations 28 and wedges 38.

Figure 4:
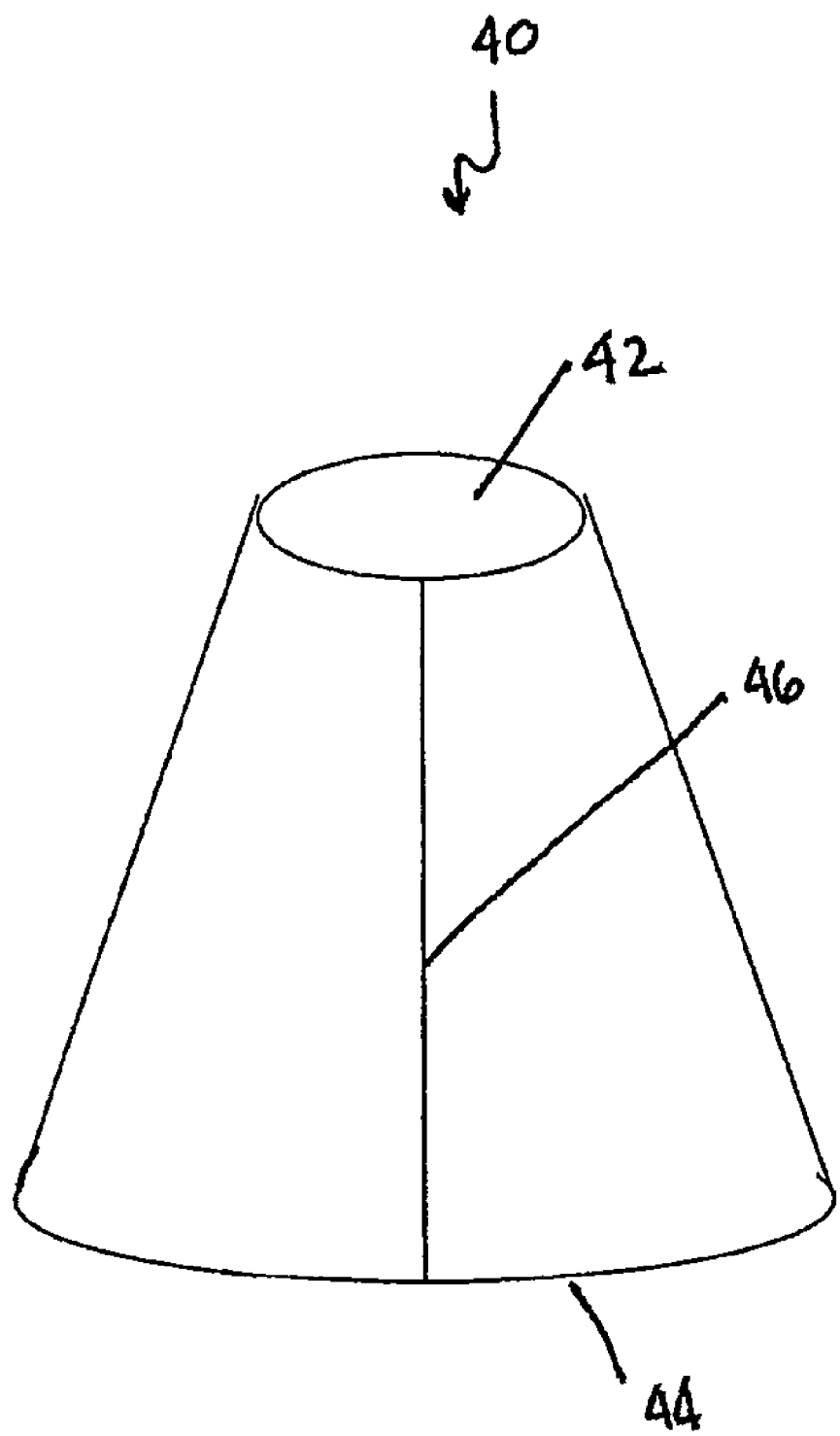
FIG. 4 illustrates a cone shaped from a backing implant in accordance with one embodiment.

Thus, the backing implant may be formed as a sheet of material that may be folded and manipulated to form a backing for complementing an acetabular cup. FIG. 4 illustrates a cone 40 formed from a backing implant as provided in FIGS. 1-3. As shown, the hole 42 forms one end of the cone. Where the implant of FIGS. 1-3 is provided without a hole 42, the cone may have a point on its end. The outer diameter of the sheet forms the other end 44 of the cone. The ends of the outer sheet corresponding to the slit overlap, or abut, to form a seam 46.

Figure 5:
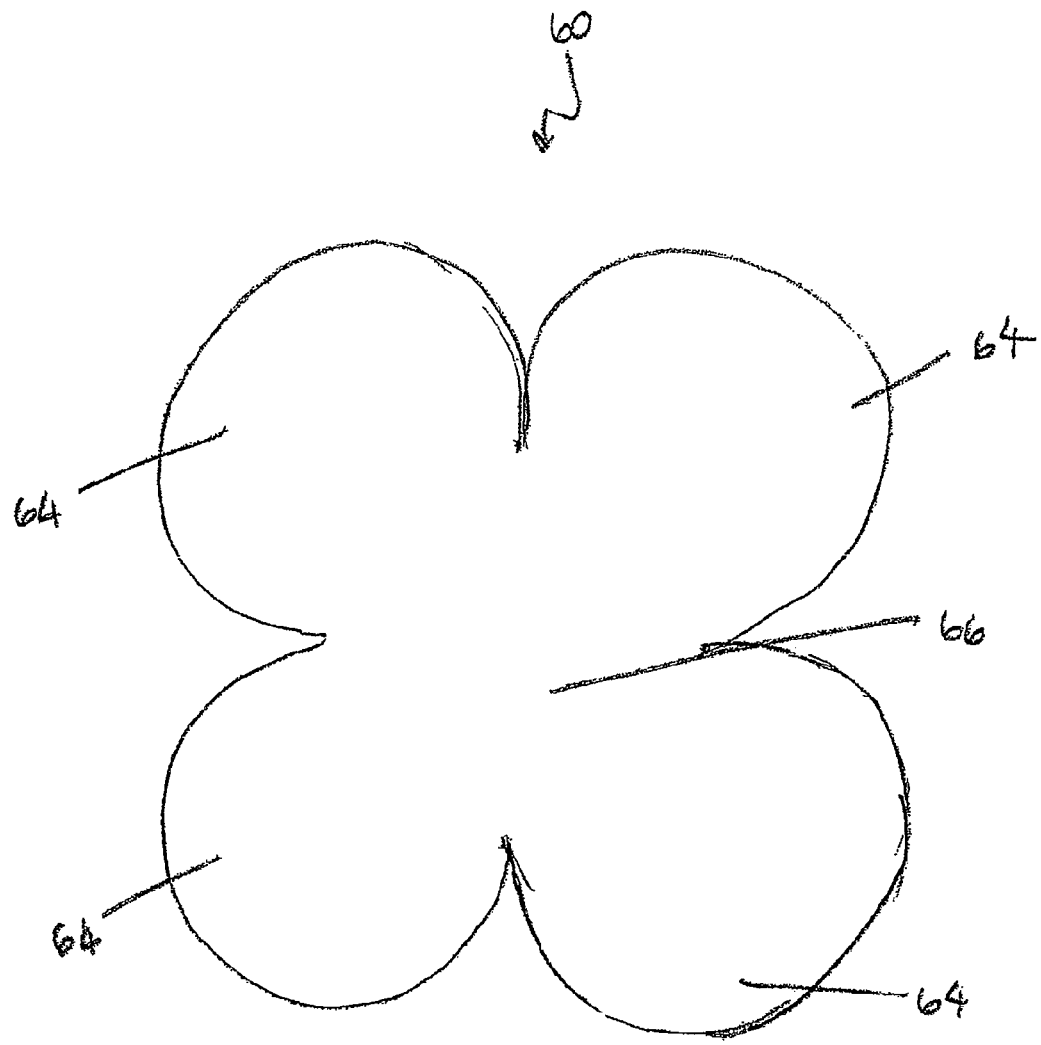
FIG. 5 illustrates a backing implant comprising four generally curved petals in accordance with one embodiment.
Figure 6:
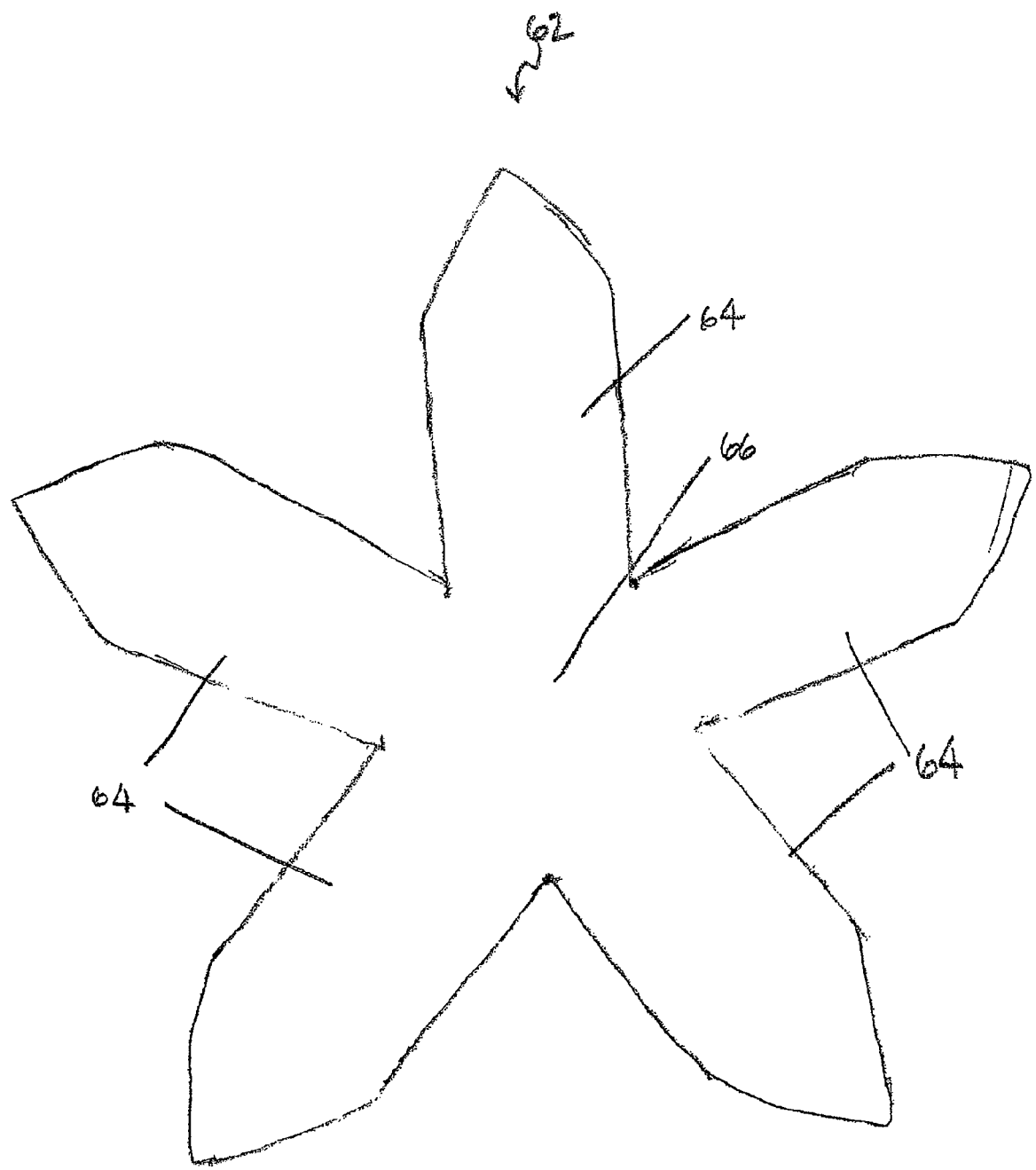
FIG. 6 illustrates a backing implant comprising five generally tipped petals in accordance with one embodiment.
Figure 7:
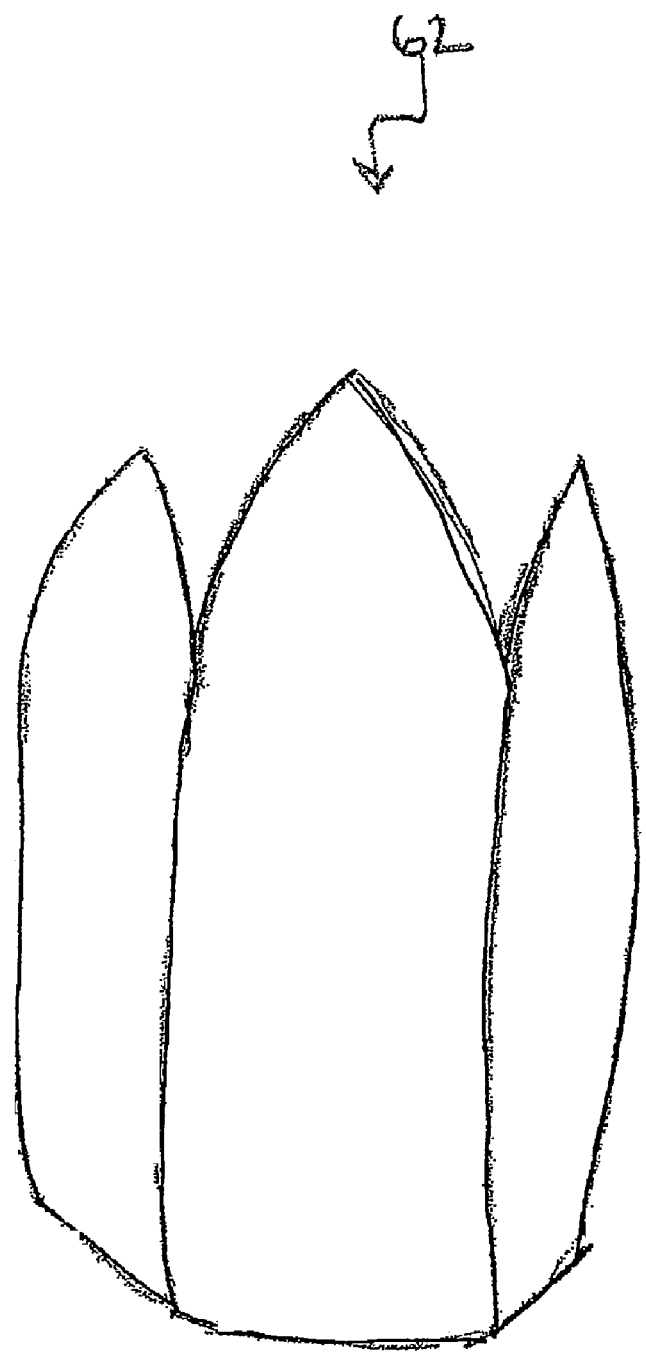
FIG. 7 illustrates the backing implant of FIG. 6 manipulated to form a backing in accordance with one embodiment.

FIGS. 5-7 illustrate a further embodiment of a backing implant. FIGS. 5 and 6 illustrate the backing implant 60 and 62, respectively, in a laid out configuration. FIG. 7 illustrates the backing implant 62 of FIG. 6 in a manipulated configuration to form a backing for complementing an acetabular cup. As shown, the backing implant 60, 62 comprises a sheet of material having a center 66 and a plurality of petals or points 64. The center 66 may be a true center of the backing implant or may merely be generally central to the petals or points 64. The petals or points 64 generally radiate from the center 66. The petals or points 64 may be manipulated toward one another to partially fold the backing implant 60, 62 in on itself. The number and shape of the petals or points 64 may be varied. In FIG. 5, four generally curved petals 64 are provided. In FIG. 6, five generally pointed petals 64 are provided. Any suitable number may be used, and they may be of any suitable shape or configuration. For use as a backing for an acetabular cup, the petals or points 64 may be folded for positioning towards the defect.

In the embodiments of FIGS. 1-3, the backing implant may be formed of a flat, flexible material that can be folded to shape. Alternatively, the backing implant may be formed of a flexible or more rigid material that is premolded to a hemispherical shape that will fit an acetabular cup. The backing implants may be supplied in a single size or a small number of sizes where the surgeon modifies or trims the backing implant to shape. Alternatively, the backing implants may be provided in a wide variety of sizes that will satisfy most requirements without modifying or trimming.

Thus, a backing implant is herein provided that comprises a generally planar sheet form that may be shaped to conform generally to an implant surface. While specific geometries are described for forming a sheet into, for example, a hemispherical shape, any suitable manner of doing so may be used. Thus, generally, the backing implant may be provided as any planar configuration that may be formed into a generally hemispherical shape. Such configurations include, for example, those that have been developed in the cartographic arts such as Cahill's butterfly, Waterman's butterfly, pseudocylindrical projections of the hemisphere, pseudoconic projections of the hemisphere, sinusoidal projections of the hemisphere, dymaxion projections of the hemisphere, other conic projections of the hemisphere, cyldinrical projections of the hemisphere, and other. As will be appreciated by one skilled in the art, the cartographic methods for converting a sphere to a planar surface may be adapted to developing a planar surface to form a hemisphere.

In some embodiments, fixation elements may be provided for fixing the backing implant to the acetabulum or other joint. For example, the backing implant may be provided with tabs, overhangs, or other structure for fixing to bone or other surface.

III. Implant Materials

The backing implant comprises a material that is formed into a generally planar configuration For ease of reference, the generally planar configuration is referred to as a sheet however such term is not intended to be limiting. The material may be osteoconductive, and also may be osteoinductive. The backing implant may be formed of a flexible material. In a further embodiment, the backing implant may be generally rigid but capable of becoming flexible when exposed to liquids such as saline or body fluids. Alternatively, other manners of providing flexibility to the material may be provided. For example, the material may be generally rigid at room temperature but flexible when heated. Alternatively, the material may comprise a reverse-phase material, such as Poloxamer 407, so that the implant is more flexible at cooler temperatures, and then firms up to become less flexible when warmed to body temperatures. In some embodiments, the backing implant may be rehydrated, for example via exposure to saline, prior to use.

To form the backing implant, the sheet may be cut using a cutting machine, using cutting molds, or in any suitable manner. In some embodiments, the material may be directly formed into the shape of the backing implant without cutting of a sheet.

Bone Particles

In one embodiment, the backing implant comprises bone matrix. The bone matrix may be provided in a particulate form, wherein the particles are of any desired size and shape. The backing implant also may comprise a sheet fabricated from, or including, elongate bone particles, such as disclosed in U.S. Pat. No. 5,507,813 for Shaped Materials Derived from Elongate Bone Particles, herein incorporated by reference. The bone particles may be obtained from cortical, cancellous and/or corticocancellous bone which may be of autogenous, allogenic, transgenic, and/or xenogenic origin.

In one embodiment, elongate bone particles used in forming the backing implant may be generally characterized as having relatively high median length to median thickness ratios, e.g., about 50:1 or about 100:1 and, similarly, relatively high median length to median width ratios, e.g., about 10:1 or about 50:1. Such particles can be readily obtained by any one of several methods, e.g., by milling or shaving the surface of an entire bone or relatively large section of bone. Thereafter, the resulting elongate bone particles may be demineralized.

Employing a milling technique, particles ranging in median length from about 2 up to about 200 mm or more (as in the case of the long bones), in median thickness from about 0.05 to about 2 mm, and in median width from about 1 to about 20 mm can be readily obtained. Depending on the procedure employed for producing the elongate bone particles, one can obtain a mass of bone particles containing at least about 60 weight percent, at least about 70 weight percent, or at least about 80 weight percent of bone particles possessing a median length of from about 2 to about 200 mm or more, or from about 10 to about 100 mm, a median thickness of from about 0.05 to about 2 mm, or from about 0.2 to about 1 mm, and a median width of from about 1 mm to about 20 mm, or about 2 to about 5 mm. These bone particles may possess a median length to median thickness ratio of 10:1, to 50:1, and up to about 500:1, or from about 10:1 to about 100:1, and a median length to median width ratio of from about 10:1 to about 200:1, or from about 50:1 to about 100:1. The bone fibers or particles of the present invention may be demineralized in any desired manner, and to any desired extent.

As descried more fully below, the bone particles can be admixed with one or more substances such as adhesives, fillers, plasticizers, flexibilizing agents, biostatic/biocidal agents, surface active agents, binding and bonding agents, fillers, and the like, prior to, during, or after shaping the particles into a desired configuration.

To prepare the backing implant, a quantity of bone particles, for example, demineralized, elongate bone particles, slurried in a suitable liquid, e.g., water, organic protic solvent, aqueous solution such as physiological saline, etc., and optionally containing one or more biocompatible ingredients such as a carrier, adhesives, fillers, plasticizers, flexibilizing agents, biostatic/biocidal agents, surface active agents, medically/surgically useful substances, etc. is applied to a form such as a flat sheet, mesh screen or three-dimensional mold and excess liquid is removed, e.g., by being drained away. This procedure is referred to herein as "wet-laying." For example, in the case of a sheet, the thickness of the layer of wetted bone particles can vary widely, e.g., from about 1 to about 40 mm. Some particle entanglement results from the wet-laying operation. Further particle entanglement, if necessary or desirable, can be effected by the use of water jets or other suitable mechanical entangling methods. Either before or after the wet-laying procedure, one or more additional substances can be added to the bone particles, e.g., thixotropic agents, therapeutic agents, and the like. The wet demineralized bone particles may then be dried, either in an oven or by lyophilization. In an alternative embodiment, the bone particles can be subjected to a compressive force, e.g., of up to about 100 psi, during and/or after the wet-laying step and/or while the drained but still wet shaped article is being dried. The resulting sheet is rigid and relatively strong when dry and flexible and pliable when wetted or hydrated.

In some embodiments, the sheet is formed by laying the DBM solution on a sieve shaped to correspond to the shape of the backing implant. Thus, for example, the sieve may be sized and shaped in a circle to correspond with the backing implant of FIG. 1.

At the site of implantation, a backing implant formed of bone particles may be employed in the dry state or, where site conformation is desired, in the hydrated state. The dry or hydrated article can be cut or sized if need be to conform to a site being repaired. The backing implant can be hydrated with a suitable biocompatible liquid, e.g., water, saline solution, etc., for a period of time ranging from about 1 to about 120 minutes. After being hydrated, the backing implant becomes flexible yet substantially retains its shape and much of its strength. The backing implant may be packaged in either the dried or wet state and stored for subsequent application. In some circumstances, the backing implant may be packaged in the wet state so that it is ready for immediate use at the surgical site.

Alternatively, the bone particles, including elongate bone particles, may be formed into a sheet that remains flexible in the dry state, for example through the addition of a plasticizer, or that is rigid and becomes flexible upon heating.

In some embodiments, the backing implant may be formed of a bone graft material having not greater than about 32% void volume formed at least in part from elongate bone-derived elements optionally in combination with bone powder. U.S. Pat. No. 6,332,779 for Method of Hard Tissue Repair discusses such bone graft material and is hereby incorporated by reference.

Other Materials

In further embodiments, the backing implant may comprise other or additional materials. For example, osteoinductive materials, such as osteoinductive proteins, may be added to the backing implant. Any suitable material may be used, but they should generally be biocompatible and lack immunogenicity. The materials may be of biological origin, such as collagen sponges, collagen fibers, etc., which may be cross-linked or otherwise processed, as desired. Other suitable biological materials, including those of allograft, autograft (e.g., iliac crest or local bone), or xenograft origin, growth factors and/or bone morphogenic proteins (including on a carrier), gelatins, hydrogels, etc., also may be used. Nonanimal biological material or synthetic materials also may be used, as desired, including silk, cotton, linen, calcium phosphate- and calcium sulfate-based materials, etc. Polymers may be used, including in combination with any of the above. Any suitable combination of the above materials may be used. The implant also may comprise synthetic materials.

In one embodiment, the backing implant comprises a polymer sheet containing calcium phosphate particles. Examples of other suitable materials include polymers, such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), minerals, etc. These may be resorbable, non-resorbable, or some of each. These materials may be used to form wicking materials, and may be synthetic, natural, etc. They may be formed as a woven material, including a braid, a nonwoven matrix, axially aligned, or in any other suitable manner.

The osteoimplant may also comprise combinations of these and other materials, and may further comprise bone, e.g., DBM fibers, DBM particles, combinations, etc.

As previously described, the backing implant may be formed of a flexible material. Such flexibility may be imparted wherein the backing implant includes a plasticizer such as glycerol. Alternatively, the backing implant may be constructed from a flexible polymer. In a further embodiment, the backing implant may be generally rigid but capable of becoming flexible when exposed to liquids such as saline or body fluids.

In alternative embodiments, the backing implant may be formed of a relatively rigid material that is premolded to a hemispherical shape.

Additives

Regardless of the material used for forming the backing implant, additional substances may be added to the material. The material used to form the backing implant may be admixed with one or more substances such as adhesives, fillers, plasticizers, flexibilizing agents, biostatic/biocidal agents, surface active agents, binding and bonding agents, fillers, and the like, prior to, during, or after shaping the particles into a desired configuration. Suitable adhesives, binding agents and bonding agents include acrylic resins, cellulosics, bioresorbable polymers such as polyglycolide, polylactide, glycolide-lactide copolymer, etc. Suitable fillers include bone powder, demineralized bone powder, hydroxyapatite, etc. Suitable plasticizers and flexibilizing agents include liquid polyhydroxy compounds such as glycerol, monacetin, diacetin, etc. Suitable biostatic/biocidal agents include antibiotics, povidone, sugars, etc. Suitable surface active agents include the biocompatible nonionic, cationic, anionic and amphoteric surfactants.

Any of a variety of medically and/or surgically useful substances can be incorporated in, or associated with the material used to form the backing implant during or after fabrication of the backing implant. Thus, for example when demineralized bone particles are used to form the material, one or more of such substances may be introduced into the demineralized bone particles, e.g., by soaking or immersing the bone particles in a solution or dispersion of the desired substance(s).

Radiopaque materials may be added to the material of the backing implant for visualization. Such materials may comprise, for example, nondemineralized bone, barium sulfate, iodine-containing compounds, titanium, or other.

Medically/surgically useful substances that can be readily combined with the demineralized bone particles and/or osteogenic material include, e.g., collagen, insoluble collagen derivatives, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), angiogenic factors, transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

A number of endogenous factors that play important roles in the development and/or repair of bone have been identified. BMPs such as BMP-2 and BMP-4 induce differentiation of mesenchymal cells towards cells of the osteoblastic lineage, thereby increasing the pool of mature cells, and also enhance the functions characteristic of differentiated osteoblasts. Canalis et al., *Endocrine Rev.* 24(2):218-235, 2003. In addition, BMPs induce endochondral ossification and chondrogenesis. BMPs act by binding to specific receptors, which results in phosphorylation of a class of proteins referred to as SMADs. Activated SMADs enter the nucleus, where they regulate transcription of particular target genes. BMPs also activate SMAD-independent pathways such as those involving Ras/MAPK signaling. Unlike most BMPs such as BMP-2 and BMP-4, certain BMPs (e.g., BMP-3) act as negative regulators (inhibitors) of osteogenesis. In addition, BMP-1 is distinct both structurally and in terms of its mechanism of action from other BMPs, which are members of the TGF-β superfamily. Unlike certain other BMPs (e.g., BMP-2, BMP-4), BMP-1 is not osteoinductive. Instead, BMP-1 is a collagenolytic protein that has also been shown to cleave chordin (an endogenous inhibitor of BMP-2 and BMP-4). Tolloid is a metalloprotease that is structurally related to BMP-1 and has proteolytic activity towards chordin. See Canalis, supra, for further details regarding the activities of BMPs and their roles in osteogenesis and chondrogenesis.

Further, other osteoinducing agents may be added to the material. These agents may be added in an activated or non-activated form. These agents may be added at anytime during the preparation of the inventive material. For example, in the case of a DBM backing implant, the osteoinducing agent may be added after the demineralization step and prior to the addition of the stabilizing agents so that the added osteoinducing agent is protected from exogenous degrading enzymes once implanted. In some embodiments the DBM is lyophilized in a solution containing the osteoinducing agent. In certain other embodiments, the osteoinducing agents are adhered onto the hydrated demineralized bone matrix and are not freely soluble. In other instances, the osteoinducing agent is added after addition of a stabilizing agent so that the osteoinducing agent is available immediately upon implantation of the DBM.

Osteoinducing agents include any agent that leads to or enhances the formation of bone. The osteoinducing agent may do this in any manner, for example, the agent may lead to the recruitment of cells responsible for bone formation, the agent may lead to the secretion of matrix which may subsequently undergo mineralization, the agent may lead to the decreased resorption of bone, etc. Suitable osteoinducing agents include bone morphogenic proteins (BMPs), transforming growth factor (TGF-0), insulin-like growth factor (IGF-1), parathyroid hormone (PTH), and angiogenic factors such as VEGF. In one embodiment, the inducing agent is genetically engineered to comprise an amino acid sequence which promotes the binding of the inducing agent to the DBM or the carrier. Sebald et al., PCT/EPOO/00637, incorporated herein by reference, describe the production of exemplary engineered growth factors suitable for use with DBM.

Any of the implants made pursuant to the teachings herein may be treated to impart, or to increase, osteoinductivity, as taught in U.S. patent application Ser. No. 11/555,606, filed Nov. 1, 2006, hereby incorporated by reference herein.

IV. Examples

Fibers are milled form human cortical shafts to a desired size range. The milled fibers are demineralized, subjected to an ethylene oxide soak as a cleansing step, and introduced to a glycerol/water solution. The fibers soak in the glycerol/water solution for a predetermined period of time. The solution containing the fibers is poured through a sheet-forming sieve. Much of the solution passes through the sieve, but the fibers and residual solution remain in a sheet-like form. The form is lyophilized, and the resulting DBM comprises a flat yet flexible consistency. A cutter is used to cut the flat form to the desired shape, such as a circular form having a diameter of 60 mm and a 5 mm hole center. The shape may be formed into a generally conical shape.

V. Conclusion

A backing implant for joint replacement is thus provided. Generally, the backing implant may be used in arthroplasty of speroidal joints such as the hip and shoulder joints, ellipsoid joints such as the radiocarpal joint, sellar joints such as the carpometacarpal joint of the thumb or the talocrural joint of the ankle, or bicondular joints such as the knee, particularly in the tibial area. The backing implant may comprise a thin sheet of material, which may be osteoconductive, and possibly osteoinductive, to thus enhance bone healing and, for cementless acetabular cups, bony integration of the acetabular cup. The backing implant may be flexible and conformable such that it may conform to irregularities in the bone of the joint and generally fill or act as a barrier to voids in the joint surface. After implantation, the backing implant may be remodeled and wholly or partially replaced by bone.

The backing implant may be used during original primary joint replacement arthroplasty or revision arthroplasty.

Although the invention has been described with reference to preferred embodiments, persons skilled in the art will recognize that changes may be made in form and detail without departing from the spirit and scope of the invention.

The invention claimed is:

1. A backing implant for repair of a joint, the backing implant comprising:
a disc formed from a coherent mass of elongate, mechanically entangled demineralized bone particles having an inner hole and an outer edge, and at least one slit extending from the inner hole to the outer edge, wherein the disc comprises a series of wedges and a breakable segment disposed around the inner hole connecting the wedges.

2. The backing implant of claim 1, wherein the disc further comprises a series of concentric perforations.

3. The backing implant of claim 1, wherein the disc is flexible.

4. The backing implant of claim 1, wherein the disc is rigid when dry and flexible when hydrated.

5. The backing implant of claim 1, wherein the disc further comprises bone growth factors.

6. The backing implant of claim 1, wherein the backing implant comprises an upper surface, morselized allograft bone being provided on the upper surface.

7. The backing implant of claim 1, wherein the hole is centered.

8. The backing implant of claim 1, wherein the implant is for repairing a socket of a ball-and-socket joint.

9. The backing implant of claim 8, wherein the socket is an acetabulum.

10. The backing implant of claim 1, wherein the demineralized bone particles are milled from human cortical shafts.

11. A backing implant for repair of a joint, the backing implant comprising:
a disc formed from a coherent mass of elongate, mechanically entangled demineralized bone particles, the disc having an interior and an outer edge, at least one slit extending from the interior to the outer edge, the disc further including at least one perforation by which the size or shape of the disc may be manipulated;
wherein the disc may be shaped into a cone and the disc comprises a series of wedges and a breakable segment disposed around the inner hole connecting the wedges.

12. The backing implant of claim 11, wherein the at least one perforation is generally concentric around the interior of the disc.

13. The backing implant of claim 12, wherein an outer diameter of the disc may be modified by perforating the disc along the at least one perforation.

14. The backing implant of claim 11, wherein the cone has a diameter that may be modified by perforating the at least one perforation.

15. The backing implant of claim 11, wherein the disc is flexible.

16. The backing implant of claim 11, wherein the disc is rigid when dry and flexible when hydrated.

17. The backing implant of claim 11, wherein the disc further comprises bone growth factors.

18. The backing implant of claim 11, wherein the disc comprises a polymer sheet containing calcium phosphate particles.

19. The backing implant of claim 11, wherein the backing implant comprises an upper surface, morselized allograft bone being provided on the upper surface.

* * * * *